US006964656B2

(12) United States Patent
Saint-Ramon et al.
(10) Patent No.: US 6,964,656 B2
(45) Date of Patent: Nov. 15, 2005

(54) SACHET FOR PACKAGING ANIMAL SEMEN AND FOR UTERINE TREATMENT

(75) Inventors: Jean-Gérard Saint-Ramon, L'Aigle (FR); Francis Lesieur, Saint-Michel Thubeuf (FR)

(73) Assignee: IMV Technologies, L'Aigle (FR)

( * ) Notice: Subject to any disclaimer, the term of this patent is extended or adjusted under 35 U.S.C. 154(b) by 353 days.

(21) Appl. No.: 10/120,134

(22) Filed: Apr. 11, 2002

(65) Prior Publication Data

US 2002/0165519 A1 Nov. 7, 2002

(30) Foreign Application Priority Data

Apr. 11, 2001 (FR) .................................. 01 04973

(51) Int. Cl.[7] ........................ A61B 19/00; A61B 17/43; B67D 5/60; B65D 83/10

(52) U.S. Cl. ........................ 604/408; 604/906; 600/35; 222/464.5; 222/523; 206/364

(58) Field of Search ................................ 604/403, 408, 604/905, 906, 262, 264, 275, 279, 187, 271; 220/62.22; 206/363–366; 383/210.1, 36; 600/35; 222/92, 634, 464.5, 521–523

(56) References Cited

U.S. PATENT DOCUMENTS 2,648,463 A * 8/1953 Scherer ...................... 222/107
3,050,060 A * 8/1962 Hoffman ...................... 600/35
5,735,401 A 4/1998 Cassou et al.
6,149,579 A * 11/2000 Lee ............................ 600/35
2003/0163110 A1 8/2003 Lecointe

FOREIGN PATENT DOCUMENTS

| | | | |
|---|---|---|---|
| EP | 0 189 702 | A1 | 8/1986 |
| EP | 0480798 | B1 | 1/1995 |
| FR | 2 778 841 | A1 | 11/1999 |
| GB | 2 342 912 | A | 4/2000 |
| WO | WO 99/59498 | A1 | 11/1999 |
| WO | WO 02/22044 | A1 | 3/2003 |

* cited by examiner

*Primary Examiner*—Patricia Bianco
*Assistant Examiner*—Leslie R. Deak
(74) *Attorney, Agent, or Firm*—Browdy and Neimark, PLLC

(57) ABSTRACT

A sachet (11) for packaging animal semen, comprising two thermoplastics material films delimiting a pocket (12) along a closed path of generally rectangular shape defining two shorter sides and two longer sides when the sachet is empty, wherein one of said shorter sides has an interruption extended by a filler conduit (14) and defining a filler area (15) in said thermoplastics material films and the other of said shorter sides has an interruption extended by a drainer conduit and defining a drainer area (17) in said thermoplastics material films, characterized in that said drainer conduit (16) has two different diameters (D1 and D2), of which the smaller diameter (D1) is at the end communicating with the interior of said sachet.

9 Claims, 1 Drawing Sheet

SACHET FOR PACKAGING ANIMAL SEMEN AND FOR UTERINE TREATMENT

Figure 1:
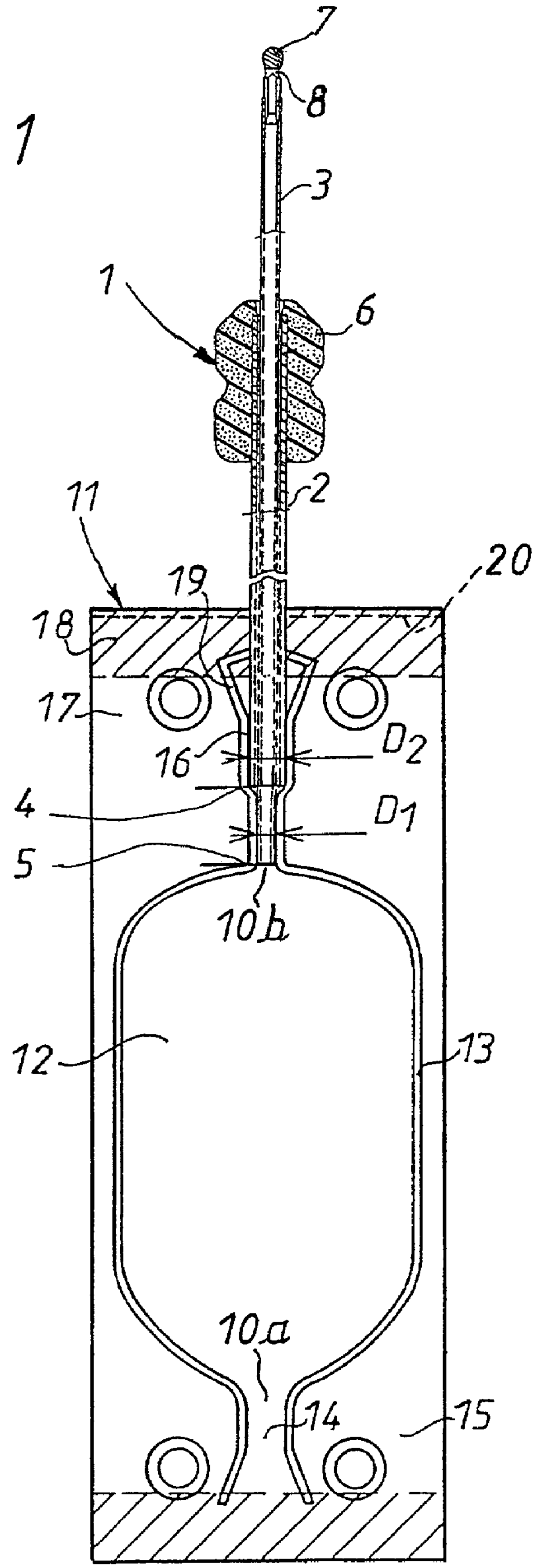

The present invention concerns a sachet for packaging animal semen. The present invention also concerns a device for animal insemination.

The sachet can be used in particular to package semen of pigs and horses but also of other species, such as rhinoceros.

A sachet for packaging liquid substances for artificially inseminating animals, in particular pigs and horses of the type also known as a dose-sachet, is well known to the person skilled in the art and is the subject matter of FR-B-2 667 504 and FR-A-2 750 399 in particular.

The sachet for packaging liquid substances for artificially inseminating animals described in FR-B-2 667 504 comprises two thermoplastics material films welded together by a weld delimiting a pocket along a closed path of generally rectangular shape defining two shorter sides and two longer sides when the sachet is empty, one of which shorter sides has an interruption, the weld defining a filler conduit running from said interruption.

Provided that they are opened correctly, the sachets described in the above reference enable rapid volumetric filling, protected from air and contamination, as well as coupling of the sachet and the tube or the probe before insemination, with reliable retention, a reliable seal, and natural and complete draining of the sachet, protected from air and from contamination. Difficulties with opening the sachets are frequently encountered, causing problems when they are used.

To use this type of sachet, which includes a filler conduit, usually extended by an insertion and centering cone for recovering or draining its contents, an opening is made in the sachet at the location of said conduit and the free end of a probe or tube is inserted into the resulting opening.

The above kind of sachet is entirely satisfactory and is still in use. However, difficulties associated with opening these sachets, which cause problems when they are used, and often necessitate the use of a tool or some other object, are nevertheless frequently encountered.

To alleviate these problems, the Applicant has developed a “peelable sachet” which is described in FR 2 750 399 and can be opened in a simple and reliable fashion without having to use any kind of tool or other object. This particular type of sachet is particularly suitable for containing animal semen and is increasingly successful.

The Applicant has also developed many devices for inseminating animals in which the neck of the uterus has rings of cartilage that are difficult to penetrate, in particular pigs. The Applicant’s patent EP-B-0 189 702 covers a telescopic gynecological probe for artificially inseminating animals such as pigs, consisting of an exterior protective sheath serving as a scabbard for a telescopic semen transfer conduit, which can move axially relative to the sheath. The sheath has a projecting end portion through which the transfer conduit passes.

The present invention is directed to render such a sachet and such a telescopic inseminator device particularly suitable for use with one another.

Further research by the Applicant has led to the development of a sachet that is particularly suitable for use with telescopic insemination or embryo transfer devices, such as that described in the patent EP-B-0 189 702, for example.

The present invention provides a sachet for packaging animal semen comprising two thermoplastics material films delimiting a pocket along a closed path of generally rectangular shape defining two shorter sides and two longer sides when the sachet is empty, wherein one of said shorter sides has an interruption extended by a filler conduit and defining a filler area in said thermoplastics material films and the other of said shorter sides has an interruption extended by a drainer conduit and defining a drainer area in said thermoplastics material films, characterized in that said drainer conduit has two different diameters, of which the smaller diameter is at the end communicating with the interior of said sachet.

The drainer conduit of the sachet according to the invention might be described as a two-stage conduit.

This particular kind of sachet leads among other things to increased accuracy in insemination operations using a telescopic device and enables each of the two tubes of different diameter of the telescopic device to be connected to the conduit of the sachet, namely the protective sheath and the transfer conduit.

In a preferred embodiment, at least one of the two thermoplastics material films has a peelable area within the drainer area.

The peelable area includes a sealing and peelable material, for example, such as a wax.

The drainer conduit can be extended by a flare, but this is not mandatory.

The two thermoplastics material films can be offset relative to each other in the drainer area, for example by approximately 2 to 3 mm.

The invention is described next in more detail, but not in any limiting manner, with reference to the accompanying FIG. 1, which is a general view of the whole of the insemination device connected to a sachet for packaging liquid substances for artificially inseminating animals and suitable for use with a telescopic insemination device.

FIG. 1 shows a sachet 11 in accordance with the invention for packaging animal semen, associated with a telescopic insemination device 1.

The sachet 11 comprises two thermoplastics material films welded together by a weld 13 delimiting a pocket 12 along a closed path of generally rectangular shape with rounded corners and defining two shorter sides and two longer sides when the sachet is empty, wherein one of said shorter sides has an interruption 10*a*, the weld defining a filler conduit 14 running from said interruption and defining in said thermoplastics films a filler area 15, and wherein the other of said shorter sides has an interruption 10*b*, the weld defining a drainer conduit 16 running from said interruption and defining in said thermoplastics material films a drainer area 17.

According to the invention, the drainer conduit 16 has two different diameters D1 and D2, of which the smaller diameter D1 is at the end communicating with the interior of the sachet.

In FIG. 1, a telescopic artificial insemination device 1 is connected to the sachet 11 of the invention.

The artificial insemination device 1 is as described in the Applicant’s patent EP-B-0 189 702 and includes a probe whose probe body consists of an exterior protective sheath 2 serving as a scabbard for a substance transfer conduit 3 able to move axially relative to said sheath inside the latter and carrying a member consisting of a spherical head 7 provided with at least one lateral evacuation orifice 8. The sheath includes a projecting head portion 6 consisting of a flexible foam plug through which the telescopic conduit 3 passes.

The exterior protective sheath 2 is crimped and sealed and inserted into the two-stage drainer conduit 16, abutting at 4 against the end of the portion of the drainer conduit 16 having the larger diameter D2.

This ensures that the required length of the end of the telescopic conduit 3 remains on the outside of the flexible foam plug 6 of the probe, which is itself placed in the neck of the uterus of the animal.

The telescopic transfer conduit 3 is also crimped and sealed into the two-stage drainer conduit 16 and locates at the end 5 of the portion of the drainer conduit 16 having the smaller diameter D1.

Thus the flexible foam plug 6 and the spherical head 7 of the telescopic conduit 3 are perfectly positioned during insemination, even if the animal moves.

In the embodiment shown, one of the two thermoplastics material films has a peelable area 18 within the drainer portion and the drainer conduit is extended by a flare 19. The flare 19 is at least partly within the peelable area. Moreover, as shown by a dashed line 20, the two plastics material films are offset relative to each other along the edge of the drainer area 17.

The person skilled in the art will understand that although the invention has been described and illustrated in terms of particular embodiments, numerous variants can be envisaged that remain within the scope of the invention as defined by the appended claims.

What is claimed is:

1. A whole device for animal artificial insemination, comprising:

a sachet for packaging animal semen and for uterine treatment, comprising two thermoplastics material films delimiting a pocket; and an insemination telescopic device comprising a protective sheath and a transfer conduit which can move relative to and inside the sheath, said transfer conduit being configured to connect to said sachet;

wherein said pocket of said sachet is delimited along a closed path of generally rectangular shape defining two shorter sides and two longer sides when said sachet is empty, wherein one of said shorter sides has an interruption extended by a filler conduit and defining a filler area in said thermoplastics material films, the other of said shorter sides has an interruption extended by a drainer conduit and defining a drainer area in said thermoplastics material films, and said drainer conduit has two different diameters, respectively, a constant diameter portion having a smaller diameter and a constant diameter portion having a larger diameter, the smaller diameter portion being at an end of the drainer conduit directly communicating with the interior of said sachet; and said telescopic device is configured to connect to said sachet with an end of said protective sheath crimped and sealed in the portion of the drainer conduit having the larger diameter whereas said transfer conduit extends outwardly from the end of the protective sheath sealed in the portion of the drainer conduit and is crimped and sealed in the portion of the drainer conduit having the smaller diameter.

2. The device claimed in claim 1, wherein at least one of said two thermoplastics material films has a peelable area within said drainer area.

3. The device claimed in claim 2, wherein said peelable area includes a sealing and peelable material.

4. The device claimed in claim 3, wherein said sealing and peelable material is wax.

5. The device claimed in claim 1, wherein said drainer conduit is extended by a flare.

6. The device claimed in claim 1, wherein said two thermoplastics material films are offset relative to each other in said drainer area.

7. The device claimed in claim 6, wherein said offset is approximately 2 to 3 mm.

8. The device claimed in claim 1, wherein an abutment is located at the end of the portion having the larger diameter and said protective sheath is adapted to abut against said abutment.

9. The device claimed in claim 1, wherein said interruption extended by a drainer conduit is defined by a weld running from said interruption.

* * * * *